United States Patent
Aires

[11] Patent Number: 5,779,481
[45] Date of Patent: Jul. 14, 1998

[54] TISSUE-ENHANCING ABUTMENT AND ADJUSTABLE COPING DEVICE FOR DENTAL IMPLANTS

[76] Inventor: Ian Aires, 4130 La Jolla Village Dr. #204, La Jolla, Calif. 92037

[21] Appl. No.: 871,935

[22] Filed: Jun. 10, 1997

[51] Int. Cl.$^6$ .................................................. A61C 8/00
[52] U.S. Cl. .................. 433/173; 433/172; 433/174; 433/177
[58] Field of Search ..................... 433/172, 173, 433/174, 177

[56] References Cited

U.S. PATENT DOCUMENTS

| | | | |
|---|---|---|---|
| 4,145,764 | 3/1979 | Suzuki et al. | 427/2 |
| 4,531,916 | 7/1985 | Scantlebury | 433/173 |
| 5,316,476 | 5/1994 | Krauser | 433/173 |
| 5,336,090 | 8/1994 | Wilson, Jr. et al. | 433/172 |
| 5,344,318 | 9/1994 | Wilson et al. | 433/177 X |
| 5,344,457 | 9/1994 | Pilliar et al. | 433/174 X |
| 5,350,302 | 9/1994 | Marlin | 433/174 |
| 5,417,570 | 5/1995 | Zuest et al. | 433/177 |
| 5,439,380 | 8/1995 | Marlin | 433/172 |
| 5,439,381 | 8/1995 | Cohen | 433/177 X |
| 5,571,016 | 11/1996 | Ingber et al. | 433/173 |

*Primary Examiner*—Nicholas D. Lucchesi
*Attorney, Agent, or Firm*—Frank G. Morkunas

[57] ABSTRACT

A tissue-enhancing adjustable device having an abutment assembly and an coronally adjustable coping assembly adapted to fit virtually all dental implant devices. The coping assembly has a rotatable coping adjuster and a threaded section thereon extending from its bottom toward its top and being in mating cooperation with a threaded bore on the abutment assembly. A tension device on the coping adjuster is adapted to exert tension on the coping assembly in an coronal direction and away from the abutment assembly at all times, particular during the adjustment process. The outer surface of the coping assembly has an annular skirt adjacent to a lower section which is of a roughened texture up to a point above the annular skirt. This facilitates better tissue growth around a post-operative site and permits adherence of tissue to the coping assembly and further permits future coronal adjustments without disturbing the tissue.

10 Claims, 3 Drawing Sheets

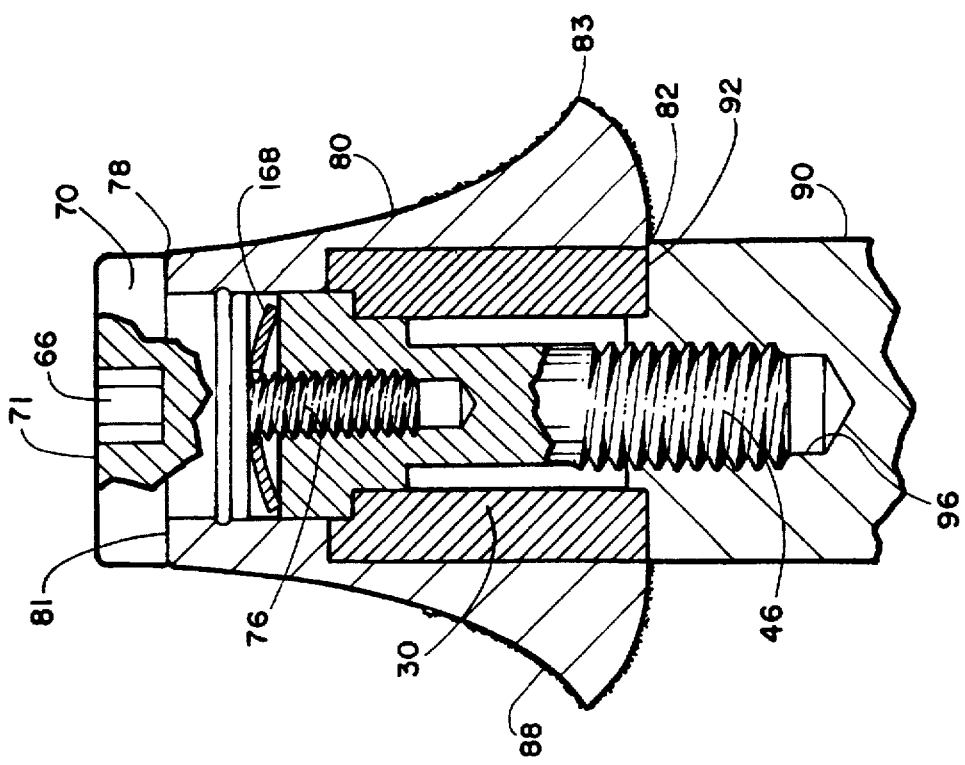
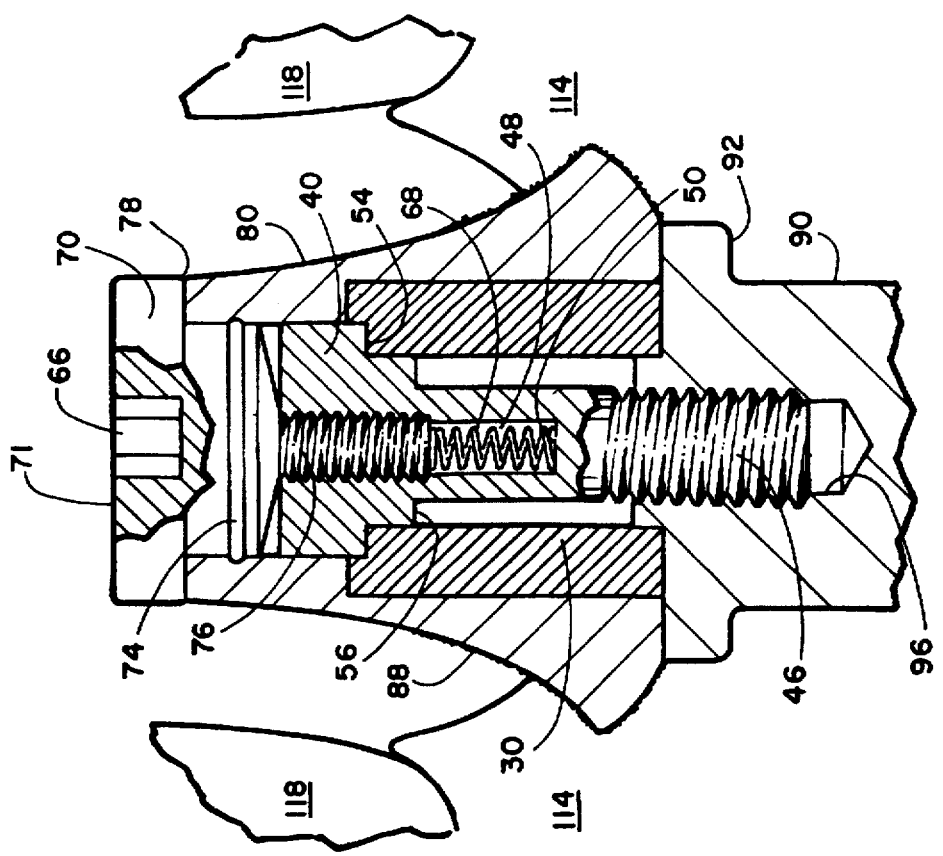

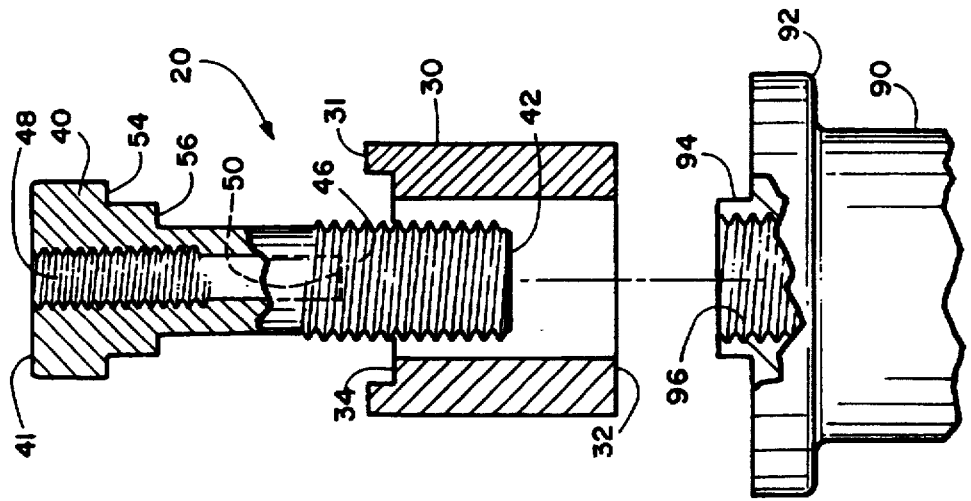
FIGURE 3A
FIGURE 4
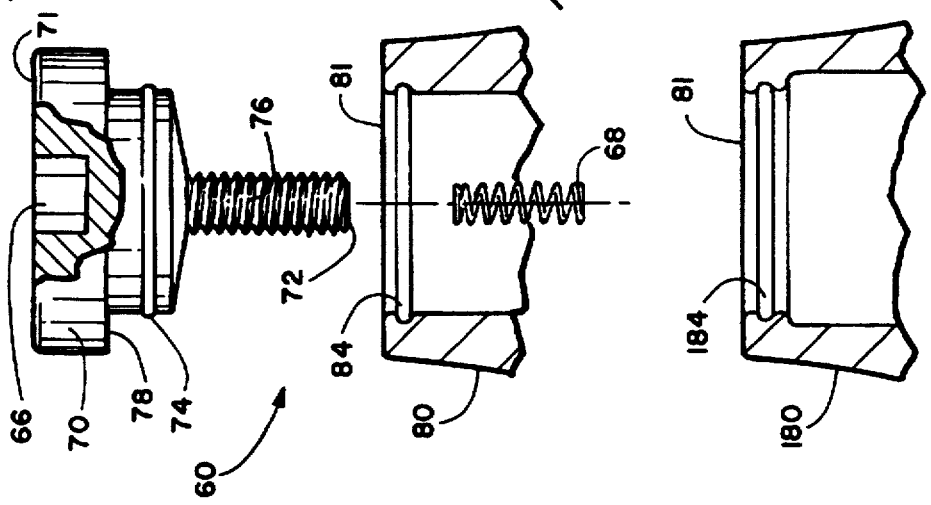
FIGURE 3B

TISSUE-ENHANCING ABUTMENT AND ADJUSTABLE COPING DEVICE FOR DENTAL IMPLANTS

BACKGROUND OF THE INVENTION

This present invention relates to an improvement in prosthodontic restoration devices, and more particularly to an implant restoration device which fosters coronal tissue growth for a more aesthetic natural gingival architecture before insertion of the implant restoration (artificial tooth).

Restorative dentistry for an edentulous patient has advanced significantly over the past years. Bone-embedded implants utilizing various posts or abutments and coping devices are virtually commonplace in the art. Two important facets to restorative dentistry remain the shape and size of the implant restoration and, more importantly, gingival architecture adjacent to the restorative site for a proper implant restoration clinical procedure. To attain adequate gingival height (gingival crest), the field has devised numerous devices and methods. Each tooth extraction results in an extraction socket or concavity in the now edentulous ridge. For purposes of this application, that socket shall be referred to as the implant site. The gingival crest at the implant site (this crest hereafter referred to as the post-operative gingival crest) is generally below the normal pre-operative gingival crest of the remaining teeth. The ability to regenerate or augment tissue in a coronal direction is more difficult to perform successfully than in any other direction. Yet it is in the coronal direction where such need exists.

While prior art patents uncovered deal with improved abutments and implants, none has the ability to enhance tissue growth in a coronally adjustable manner to achieve a more consistent post-operative gingival crest in relation to the pre-operative gingival crest as does the present invention. Presently the only way to enhance the gingival tissue is through a surgical procedure; i.e., a gingival graft taken from some part of the mouth, usual the hard palate. Even with surgery, obtaining a well shaped gingival architecture, specifically the papilla, is difficult, if not impossible Pat. No. 5,316,476 issued to Krauser describes a dental implant for holding a dental prosthesis in place after implantation into a bone. This implant has shallow circumferential grooves to permit bone to grow entirely therein such that the bone adheres thereto. A cap is attached to the implant. It has as outward expanding truncoconical head and is left in place to keep the upper portion of the implant free of tissue and ready for the attachment of the prothesis.

Pat. No. 5,344,457 issued to Pilliar, et.al., also relates to an implant anchored into bone and/or fibrous tissue to which a prothesis may be attached. The implant has a lower region and an upper region. The lower region is attached to bone. It has a porous surface into which bone may grown thereby anchoring the implant thereto. In one embodiment the upper region is coated with a bioreactive coating to allow direct bonding of bone and/or gingival tissue and to inhibit apical epithelial migration.

U.S. Pat. No. 5,350,302 issued to Marlin describes abutments posts, gingival collars, and universal adapters with fixation screws for use with dental implants. The top of the adaptor has an indexed projection, the gingival collar is also indexed. The respective indexing provides for angle correction in the horizontal plane by the counter-rotation of the gingival collar and the head of the post. The post head has a variety of angles to facilitate vertical angle correction where necessary. The angle-correcting features (horizontal and vertical) allow for precise overall angle correction of implant placement.

U.S. Pat. No. 5,571,016 issued to Ingber, et.al., describes a bone-embedded implant having an abutment post through which a variety of arrangements and types of prosthetics may be supported. This abutment also supports the use of separate copings. The abutment further has an access bore to accommodate threaded screw fasteners which carry a deformable washer and are adapted to hold the dental implant as assembled and to seal the gingival tissue region into which the abutment post is fitted.

None of these prior art inventions accommodates or facilitates coronal gingival marginal growth about the implant site; nor, and more importantly, do any of the prior art inventions provide for an adjustability to such growth.

Accordingly, several objects and advantages of my invention are:
- to facilitate gingival tissue growth concentrically and coronally;
- to provide for coronal adjustment of gingival growth while simultaneously preventing lateral dislodgement of such growth;
- to provide for fabrication of the device to fit different kinds, types, sizes, and shapes of implant bodies; and
- to realize a final aesthetic gingival sculpting after completion of the prosthetic restoration.

Any abutment and implant device may be adapted for use in conjunction and/or combination with the adjustable coronal tension-exerting coping of the present invention. The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF SUMMARY OF THE INVENTION

The above-noted problems, among others, are overcome by the present invention. Briefly stated, the present invention has an abutment assembly and a coping assembly which fosters and facilitates tissue growth, is adjustable, and is suited for dental implants. The abutment assembly comprises an abutment member, an abutment anchoring means for anchoring the abutment assembly into an implant with the anchoring means having a threaded abutment bore terminating at a ledge therein, and a coupling means for coupling the abutment member to the abutment anchoring means. The coping assembly has a rotatable coping adjuster and a threaded section thereon extending from its bottom toward its top and being in mating cooperation with the threaded bore. A tension means on the coping adjuster is adapted to exert tension on the coping assembly in an opposing direction from the abutment assembly. The coping member has an outer surface having an annular skirt adjacent to a lower section and a roughened texture thereon to a point adjacent to the annular skirt, for the purpose of facilitating tissue growth. It further has a coupling means for coupling the coping adjuster onto the coping member. The adjuster permits a coronal movement of the coping assembly as tissue grows and adheres to the roughened section.

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 1 is cross-section elevation view of the tissue-enhancing abutment and adjustable coping device seated in an implant site.

FIG. 2 is a cross-section elevation view of a second embodiment of the tissue-enhancing abutment and adjustable coping device seated in an implant site.

FIG. 3A is an exploded partial break-away elevation view of the coping assembly.

FIG. 3B is a partial cross-sectional view of a second embodiment of the coping assembly.

FIG. 4 is an exploded partial break-away elevation view of the healing abutment assembly.

DETAILED DESCRIPTION OF THE INVENTION

Figure 5:
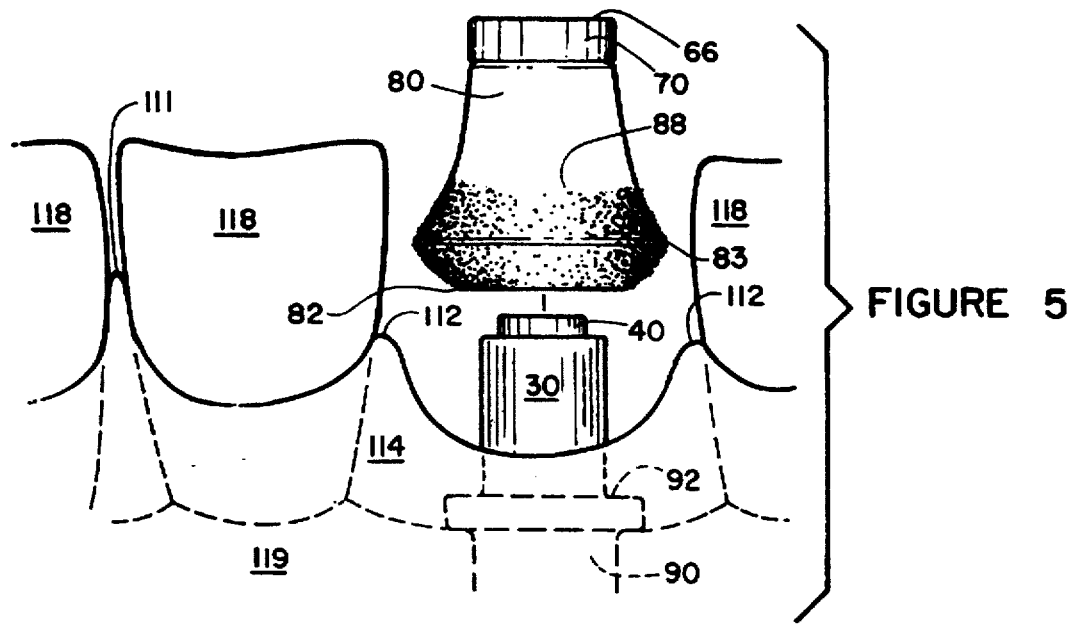
FIGS. 5 through 7 are elevation views of the tissue-enhancing abutment and adjustable coping device before insertion, during initial insertion, and after significant post-operative gingival growth, respectively.

Referring now to the drawings in detail, which are not to scale but are drawn for ease of understanding the invention, and in particular to FIGS. 1 and 4, the tissue-enhancing abutment and adjustable coping device constructed in accordance with a preferred embodiment of the present invention is seated on top of implant 90. The device is comprised of a healing abutment assembly 20 having an abutment member 30 which is substantially cylindrical and seated on the implant 90, said implant 90 having an implant ledge 92 and a threaded implant bore 96. The abutment member 30 is secured to the implant 90 by an an anchoring means. In the embodiment shown, the anchoring means comprises an abutment screw 40. Abutment screw 40 has an abutment screw top 41, abutment screw bottom 42, and abutment screw threading 46 threaded substantially from the abutment screw bottom 42 toward the abutment screw top 41. From the abutment screw top 41, substantially centered thereon, is an abutment bore 48 which is threaded. The abutment bore 48 extends downward terminating at an abutment ledge 50 contained within the abutment bore 48.

Below the head of the abutment screw 40 are a first step 54 and a second step 56. In use, the abutment member 30 is placed on the implant ledge 92. The abutment screw threading 46 is in mating cooperation with the implant bore threading 96. The abutment screw 40 is tightened and secured to the implant 90 by these cooperating threads. In one embodiment of the invention, as the abutment screw 40 is tightened, the first step 54 comes to securely rest on the abutment recess 34 adjacent to and below the abutment member top 31. In yet another embodiment, it can rest on the abutment member top 31. The second step 56 and the coronal hex 94 of the implant 90 each abut the inner walls of the abutment member 30. By this process, the healing abutment assembly 20 is secured to the implant 90. This is referred to as the abutment assembly coupling.

Referring now to FIGS. 1 and 3A, the device further has a coping assembly 60 which seats on top of and over the healing abutment assembly 20. The coping assembly 60 has a coping member 80 into which a coping screw 70 is rotatably connected. The coping screw 70 has a coping screw top 71 and a coping screw bottom 72. More generally, this may be referred to as the coping adjuster which has a coping adjuster top and a coping adjuster bottom. The underside of the coping screw top has a coping screw step 78. From the coping screw bottom 72 and substantially upward, the coping screw is threaded 76. The coping screw threading 76 is in mating cooperating with the threading within the abutment screw bore 48. Horizontally encircling an area below the coping screw step 78 is a coping screw ring 74.

The coping member 80 has a coping member top 81 and a coping member bottom 82. Adjacent to the coping member top 81 and within the inner walls of the coping member a channel 84 is formed. As shown in FIG. 3A, this channel 84 may be formed within the inner wall of the coping member 80; or, as shown in FIG. 3B, the channel 184 may be formed by two opposing protrusions on the inner wall of the coping member 180. The respective channels are adapted to rotatably accept, mate with, and retain the coping screw ring 74 thereby rotatably securing the coping screw 70 to the coping member 80. This is referred to as the coping assembly coupling means. Below the coping screw ring 74, the inner walls of the coping member 80 overlay and slidingly abut the outer walls of the abutment member 30.

Once the healing abutment assembly 20 is in place, the coping assembly 60 is mated with the healing abutment assembly 20 by mating and tightening the coping screw 70 (or adjuster) into the abutment bore 48. The coping screw bottom 72 is substantially less in length than is the abutment bore 48 such that the coping screw bottom 72 does not touch the abutment ledge 50 therein. Although the mating of the healing abutment assembly 20 with the coping assembly 60 is secure when so tightened, when coronal adjustments are made, tolerances within the respective threads prevents a completely static fit; the two assemblies are subject to some play or movement. Such play or movement vertically militates against optimum coronal gingival growth and is counterproductive to coronal growth and maintenance. Given the minute distances with which we are dealing, even minimal movement is counterproductive to optimal coronal gingival growth.

To mitigate this movement, I have devised a tension means to cooperate with the two assemblies in opposing directions. One embodiment of this tension means is shown in FIG. 1. It consists of a bias member or spring 68 adjacent to the coping screw bottom 72. The spring 68 is attached to the coping screw bottom 72 and is of sufficient length and tension to forcefully rest on the abutment ledge 50 within the abutment bore 48. When initially inserted, the coping screw 70 seats onto the healing abutment assembly 20. As tissue growth begins and increases, the objective then is to facilitate coronal movement of the tissue. This is accomplished by unscrewing, minimally and in suitable increments, the coping screw 70. When this is done, the initial tight fit between coping screw and the abutment screw top 71 is destroyed. Once this is effected, as explained above, the vertical movement associated with the tolerances relative to the respective threads is realized. The force of the spring 68 in opposing directions maintains the coronal distance integrity of the coping assembly 60 from the healing abutment assembly 20 and prevents any undesired movement, retreat, or dislodging of the growing tissue.

FIG. 2 shows a second embodiment of this tension means to be a biasing washer (or a Belleville-like washer) 168 as the bias member. It is attached in between the coping screw 70 and the abutment screw top 41. The spring 68 of the previous embodiment is not necessary in this embodiment, though it may be used as a complement thereto. As the coping screw 70 is unscrewed from its initial tight fit, the Belleville-like washer 168 forces the coping screw 72 upward from the healing abutment assembly 20 thereby maintaining coronal distance integrity of the device.

To make these coronal adjustments, I have included in my device, on the coping screw top 71 a coping adjustment member 66. This is a standard slotted, hexed, or similarly shaped adjustment member suited to accept a mating adjustment tool (not shown) and to screw-in or un-screw the coping assembly 60 into or out from the healing abutment assembly 20.

The shape, texture, and dimensions of the outer surface of the coping member 80 are important features to further facilitate gingival growth overall and, coronally in particular. The total length of the exterior of the coping is generally about 6 mm to 8 mm. This includes both a smooth surface and a roughened surface 88. The exterior surface below the smooth surface is a semi-rough surface as denoted by reference numeral 88 in FIGS. 1 and 2 (refer also to FIGS. 5 and 6). This roughened (or rough) surface ranges in height from about 1.5 mm to about 3.0 mm. A titanium-plasma spray may be used to establish this semi-rough surface although any similar such spray or compound, suited for the intended purpose, may be used. The function of the semi-rough surface is to facilitate and foster soft tissue, after it grows post-operatively, to adhere to it.

The smooth surface ranges in height from about 5 mm to about 5.5 mm. Any material such as, but not limited to, titanium, may be used for the smooth surface. The function of this smooth exterior surface is to prevent excess tissue inflammation at the gingival margin area. Any smooth-like material suited for the intended purpose will suffice. The coping member 80 also has an annular skirt 83 there around located substantially above the coping member bottom 82. An upper section is defined on the exterior surface of the coping member 80 at a point above the annular skirt 83. A lower section is defined at a point below the annular skirt 83.

The combination of the smooth surface and the rough surface encourages direct mechanical attachment of the tissue to the rough surface and permits the growing tissue to closely approximate or touch the smooth surface but not to mechanically adhere to it.

The unique outward flanged contour of the upper section of the coping member 80, which terminates at the annular skirt 83 and recedes radially inward therefrom to the coping member bottom 82, further facilitates tissue growth, especially from below the underside of the coping member 80, and attachment of all surrounding tissue growth to the coping member 80. As seen in FIG. 2, the flange terminates at the coping skirt 83, an annular skirt adjacent to the coping member bottom 82. As indicated above, from the coping skirt 83 on down, the exterior surface of the coping member 80 retreats radially inward terminating at point located at the coping member bottom 82 in close relationship to the perimeter of the implant ledge 92.

The contour of the coping member 80 as well as the rough surface thereof are important for good tissue adherence and growth. Good adherence and growth can be achieved where the vertical dimension of the lower section in relation to the overall height of the coping member bears a ratio of between about 1.0:4.5 to about 1.0:6.0. Better results are achieved with ratios from between about 1.0:2.8 to about 1.0:3.5. Best results can be achieved with ratios from between about 1.0:2.6 to about 1.0:2.3. Additionally, good tissue adherence and growth can be achieved where the vertical dimensions of the smooth surface in relation to the rough surface of the coping member bears a ratio of between about 1.00:0.27 to about 1.00:0.60. Better results are achieved with ratios from between about 1.00:0.30 to about 1.00:0.50. Best results can be achieved with ratios from between about 1.00:0.35 to about 1.00:0.40.

Once the tissue adheres, the coping assembly 60 can be adjusted vertically away from the healing abutment assembly 20 in suitable increments as warranted by the circumstances and desired result. The tension means (spring 68 or Bellville-like washer 168) keeps the adjustment of the device coronally forced and prevents any reverse movement due to play associated with the tolerances of the abutment bore threading 48 and the coping screw threading 76. The tension means facilitates a smooth, unabated coronal adjustment bringing with it, the tissue attached to the rough surface 88 of the coping member 80. The coping screw ring 74 and mating coping channel 84 or 184 permits rotation of the coping screw 70 without tandem rotation of the coping member 80. Such rotation of the coping member 80 would weaken the attached tissue and, possibly, dislodge it. This tension means assists in forcing a perpetual coronal movement of the coping assembly 60 regardless of whether or not the device is being adjusted. The tension exists at all times.

Figure 6:
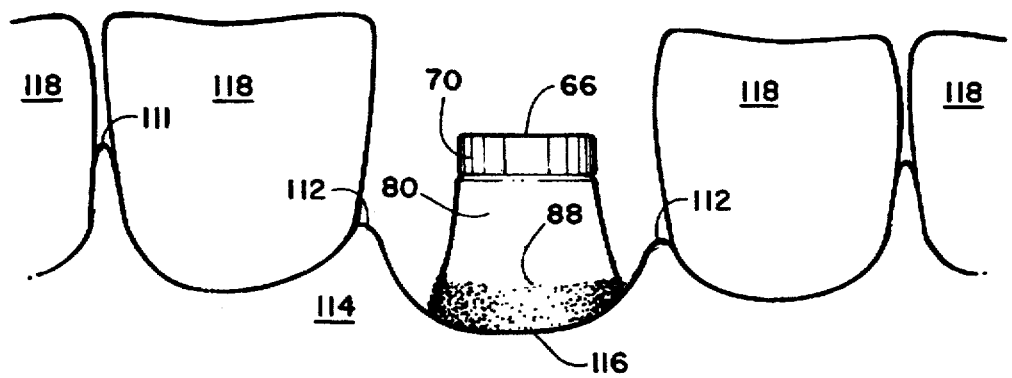
Figure 7:
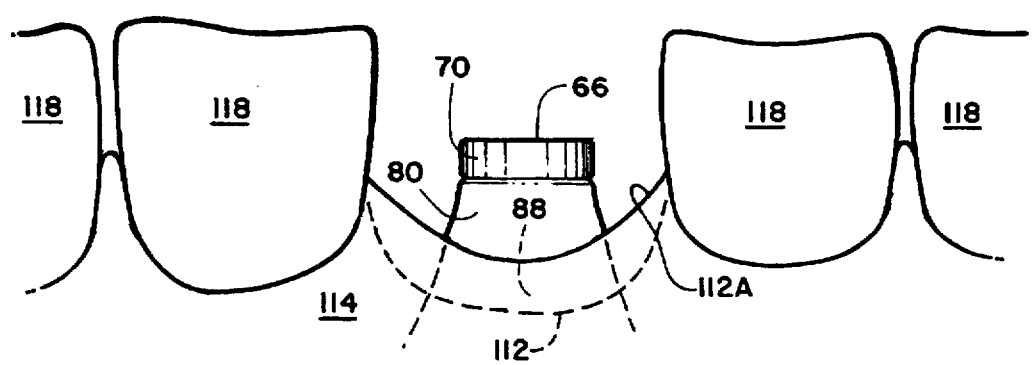

FIGS. 5 through 7 show the coping assembly 60 inserted over the abutment member 30 and the follow-on tissue growth and associated gingival crests. Pre-operative gingival crest 111 is between a patient's teeth 118. The implant 90 is anchored to a patient's bone 119. Tissue 114 covers the lower portion of the teeth 118. The extraction site, referred to as the implant site 116, reveals a post-operative gingival crest 112 as substantially lower that the pre-operative gingival crest 111. The device used a directed facilitates the coronal extension of the gingival crest 112A from within and around the implant site as depicted in FIG. 7. The phantom line denotes the original post-operative gingival crest.

Once tissue grows and adheres to the lower section, the coping member 80 is again adjusted coronally. The 'void' created by the stretched tissue is filled by additional tissue as a result. By repeating this procedure, the post-operative gingival crest can be substantially moved coronally to a crest substantially near in height as the pre-operative gingival crest. Such continued and repeated adjustment also fortifies previously grown tissue. After sufficient soft tissue has adhered and stabilized, the coping assembly 60 is removed from the healing abutment assembly 20. This is accomplished by use of a cutting tool to release the soft tissue attached to the coping member 80. A special such tool, fitting the coping member 80 cuts and releases the tissue therefrom. A clean cut is made, the tissue left relatively intact at a suitable post-operative gingival crest.

A temporary tissue maintenance cover screw having a design and shape similar to the coping, but with a smooth surface, is then inserted onto the abutment to maintain the new tissue position during the fabrication of the implant restoration. Thereafter the implant restoration is inserted onto the abutment assembly 20 having sufficient soft tissue therearound to render a substantially uniform gingival crest appearance throughout.

The present disclosure includes that contained in the present claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention. Accordingly, the scope of the invention should be determined not by the embodiment[s] illustrated, but by the appended claims and their legal equivalents.

The invention claimed is:

1. A tissue-enhancing abutment and adjustable coping device for dental implants comprising:
   a. an abutment assembly having
      (1) an abutment member with an abutment member top and an abutment member bottom;
      (2) an abutment anchoring means for anchoring said abutment assembly into an implant, said abutment anchoring means further having a threaded abutment bore therein terminating at an abutment ledge;
      (3) an abutment assembly coupling means for coupling said abutment member to said abutment anchoring means;
   b. a coping assembly having
      (1) a rotatable coping adjuster, said coping adjuster having a coping adjuster top, a coping adjuster bottom, a threaded section extending from the coping adjuster bottom toward the coping adjuster top and in mating cooperation with said threaded abutment bore, a coping tension means on said coping adjuster, said tension means exerting tension on said coping assembly in an opposing direction from said abutment assembly; and
      (2) a coping member having a coping member top, a coping member bottom, an outer surface, and a coping assembly coupling means adjacent to said coping member top for coupling said coping adjuster onto said coping member, said outer surface further comprising an upper section and a lower section, said lower section having a substantially roughened texture thereon; whereby when said abutment assembly is anchored to said implant by said anchoring means, and said coping assembly is affixed to said abutment assembly by mating of the coping adjuster with the threaded abutment bore, said tension means establishes a coronal tension on said coping assembly which, by said coping adjuster may be further adjusted coronally to accommodate a coronal movement of tissue bonding to said lower section of said coping member to further facilitate tissue growth and coronal buildup.

2. The device as defined in claim 1 wherein said coping member further comprises a flanged annular skirt substantially adjacent to said lower section encircling said coping member and radially receding inward and downward thereafter.

3. The device as defined in claim 2 wherein said annular skirt is configured at a point such that it bears a ratio of between about 1.0:4.5 to about 1.0:6.0 as established between a vertical dimension from said annular skirt to said coping member bottom and an overall vertical dimension of the coping member.

4. The device as defined in claim 1 wherein said upper section in relation to said lower section bears a ratio of between about 1.00:0.27 to about 1.00:0.60.

5. The device as defined in claim 1 wherein said tension means comprises a coping spring on the coping adjuster bottom which biasedly cooperates with the abutment ledge.

6. The device as defined in claim 1 wherein said coping assembly coupling means comprises a channel adjacent to the coping member top and a mating coping screw ring on said coping adjuster adjacent to said coping adjuster top for rotatably holding said coping adjuster onto said coping member.

7. The device as defined in claim 1 wherein said anchoring means comprises an abutment screw for screwing into the implant bore, said abutment screw having an abutment screw top, an abutment screw bottom, with said threaded abutment bore extending from the abutment screw top downward terminating substantially above the abutment screw bottom at the abutment ledge.

8. The device as defined in claim 7 wherein said tension means comprises a biased member substantially below the coping adjuster top and in biased communication with said abutment screw top.

9. The device as defined in claim 7 wherein said abutment screw further comprises a first step adjacent to the abutment screw top, and a second step below the abutment screw top, said first step seating with said abutment member top to thereby hold said abutment member onto said implant.

10. The device as defined in claim 7 wherein said abutment member further comprises an abutment recess adjacent to the abutment member top and said abutment screw further comprising a first step adjacent to the abutment screw top, and a second step below the abutment screw top, said first step seating with said abutment recess to thereby hold said abutment member onto said implant.

* * * * *